US008522785B2

(12) United States Patent
Berthon-Jones et al.

(10) Patent No.: US 8,522,785 B2
(45) Date of Patent: Sep. 3, 2013

(54) INEXTENSIBLE HEADGEAR AND CPAP OR VENTILATOR MASK ASSEMBLY WITH THE SAME

(75) Inventors: Michael Berthon-Jones, Leonay (AU); Michael Kassipillai Gunaratnam, Marsfield (AU); Peter Edward Bateman, Cherrybrook (AU); Philip James Jenkinson, Epping (AU); Gordon Joseph Malouf, Gymea Bay (AU)

(73) Assignee: ResMed Limited, Bella Vista (AU)

( * ) Notice: Subject to any disclaimer, the term of this patent is extended or adjusted under 35 U.S.C. 154(b) by 2329 days.

(21) Appl. No.: 10/523,607

(22) PCT Filed: Aug. 5, 2003

(86) PCT No.: PCT/AU03/00988
§ 371 (c)(1),
(2), (4) Date: Mar. 10, 2005

(87) PCT Pub. No.: WO2004/012803
PCT Pub. Date: Feb. 12, 2004

(65) Prior Publication Data
US 2006/0118119 A1 Jun. 8, 2006

Related U.S. Application Data

(60) Provisional application No. 60/400,686, filed on Aug. 5, 2002.

(51) Int. Cl.
| | |
|---|---|
| *A61M 16/00* | (2006.01) |
| *A61M 15/08* | (2006.01) |
| *B63C 11/02* | (2006.01) |
| *A62B 18/00* | (2006.01) |
| *A62B 29/00* | (2006.01) |
| *A62B 99/00* | (2009.01) |
| *A62B 18/08* | (2006.01) |
| *A62B 17/04* | (2006.01) |
| *A62B 7/10* | (2006.01) |
| *A62B 19/00* | (2006.01) |
| *A62B 23/02* | (2006.01) |
| *F24F 13/00* | (2006.01) |

(52) U.S. Cl.
USPC ............ 128/207.11; 128/200.26; 128/200.27; 128/200.28; 128/200.29; 128/201.13; 128/201.14; 128/201.19; 128/201.22; 128/201.23; 128/201.25; 128/201.26; 128/201.27; 128/202.28; 128/203.23; 128/203.29; 128/204.18; 128/204.26; 128/205.13; 128/205.25; 128/206.12; 128/206.17; 128/206.21; 128/206.24; 128/206.28

(58) Field of Classification Search
USPC ............ 128/200.26, 200.27, 200.28, 200.29, 128/201.13, 201.14, 201.19, 201.22, 201.23, 128/201.24, 201.25, 201.26, 201.27, 202.28, 128/203.23, 203.29, 204.18, 204.26, 205.13, 128/205.25, 206.12–206.17, 206.21–207.12
See application file for complete search history.

(56) References Cited

U.S. PATENT DOCUMENTS

| | | |
|---|---|---|
| 781,516 A | 1/1905 | Guthrie |
| 812,706 A | 2/1906 | Warbasse |

(Continued)

FOREIGN PATENT DOCUMENTS

| | | |
|---|---|---|
| AU | 59430/94 | 10/1995 |
| DE | 19817332 A1 | 1/1999 |

(Continued)

OTHER PUBLICATIONS

International Search Report for PCT/AU2003/000988, Mailed Oct. 9, 2003, 5 pages.

(Continued)

*Primary Examiner* — Patricia Bianco
*Assistant Examiner* — Brandon L Jackson
(74) *Attorney, Agent, or Firm* — Nixon & Vanderhye P.C.

(57) ABSTRACT

A headgear (200) for a respiratory mask (202) of a ventilator or CPAP device is provided. The headgear includes a strap portion (204, 206) formed of a substantially inextensible material. The strap portion has formed on one end thereof a connecting structure configured to connect to a mask of the ventilator or CPAP device. One advantage is that the mask will not or at least will be less inclined to lift off the face as mask pressure is increased.

28 Claims, 17 Drawing Sheets

(56) References Cited

U.S. PATENT DOCUMENTS

| | | |
|---|---|---|
| 1,081,745 A | 12/1913 | Johnston et al. |
| 1,192,186 A | 7/1916 | Greene |
| 1,653,572 A | 12/1927 | Jackson |
| 1,926,027 A | 9/1933 | Biggs |
| 2,123,353 A | 7/1938 | Catt |
| 2,248,477 A | 7/1941 | Lombard |
| 2,254,854 A | 9/1941 | O'Connell |
| 2,317,608 A | 4/1943 | Heidbrink |
| 2,353,643 A | 7/1944 | Bulbulian |
| 2,371,965 A | 3/1945 | Lehmberg |
| 2,376,871 A | 5/1945 | Fink |
| 2,383,649 A | 8/1945 | Heidbrink |
| 2,415,846 A | 2/1947 | Randall |
| 2,438,058 A | 3/1948 | Kincheloe |
| 2,578,621 A | 12/1951 | Yant |
| 2,823,671 A | 2/1958 | Garelick |
| 2,931,356 A | 4/1960 | Schwarz |
| D188,084 S | 5/1960 | Garelick |
| 2,939,458 A | 6/1960 | Lundquist |
| 2,974,665 A | 3/1961 | Motsinger |
| 3,013,556 A | 12/1961 | Galleher, Jr. |
| 3,182,659 A | 5/1965 | Blount et al. |
| 3,189,027 A | 6/1965 | Bartlett |
| 3,193,624 A | 7/1965 | Webb et al. |
| 3,238,943 A | 3/1966 | Holley |
| 3,315,674 A | 4/1967 | Bloom et al. |
| 3,330,273 A | 7/1967 | Bennett |
| 3,362,420 A | 1/1968 | Blackburn et al. |
| 3,363,833 A | 1/1968 | Laerdal |
| 3,556,122 A | 1/1971 | Laerdal |
| 3,580,051 A | 5/1971 | Blevins |
| 3,700,000 A | 10/1972 | Hesse et al. |
| 3,720,235 A | 3/1973 | Schrock |
| 3,796,216 A | 3/1974 | Schwarz |
| 3,799,164 A | 3/1974 | Rollins |
| D231,803 S | 6/1974 | Huddy |
| 4,077,404 A | 3/1978 | Elam |
| D250,131 S | 10/1978 | Lewis et al. |
| 4,167,185 A | 9/1979 | Lewis |
| 4,226,234 A | 10/1980 | Gunderson |
| 4,245,632 A | 1/1981 | Houston |
| D262,322 S | 12/1981 | Mizerak |
| 4,304,229 A | 12/1981 | Curtin |
| 4,328,797 A | 5/1982 | Rollins, III et al. |
| 4,347,205 A | 8/1982 | Stewart |
| 4,354,488 A | 10/1982 | Bartos |
| 4,402,316 A | 9/1983 | Gadberry |
| 4,412,537 A | 11/1983 | Tiger |
| 4,467,799 A | 8/1984 | Steinberg |
| 4,522,639 A | 6/1985 | Ansite et al. |
| 4,537,192 A | 8/1985 | Foster |
| 4,558,710 A | 12/1985 | Eichler |
| 4,616,647 A | 10/1986 | McCreadie |
| 4,622,964 A | 11/1986 | Flynn |
| 4,623,573 A | 11/1986 | Katz |
| 4,655,213 A | 4/1987 | Rapoport et al. |
| 4,665,570 A | 5/1987 | Davis |
| 4,668,325 A | 5/1987 | Katz |
| 4,671,271 A | 6/1987 | Bishop et al. |
| 4,677,975 A | 7/1987 | Edgar et al. |
| 4,677,977 A | 7/1987 | Wilcox |
| 4,704,172 A | 11/1987 | Katz |
| D293,613 S | 1/1988 | Wingler |
| 4,739,755 A | 4/1988 | White et al. |
| 4,770,169 A | 9/1988 | Schmoegner et al. |
| 4,774,941 A | 10/1988 | Cook |
| 4,778,706 A | 10/1988 | Katz |
| 4,782,832 A | 11/1988 | Trimble et al. |
| 4,799,477 A | 1/1989 | Lewis |
| 4,809,692 A | 3/1989 | Nowacki et al. |
| 4,819,629 A | 4/1989 | Jonson |
| 4,821,713 A | 4/1989 | Bauman |
| 4,841,953 A | 6/1989 | Dodrill |
| 4,848,334 A | 7/1989 | Bellm |
| 4,848,366 A | 7/1989 | Aita et al. |
| 4,907,584 A | 3/1990 | McGinnis |
| 4,910,806 A | 3/1990 | Baker et al. |
| 4,919,128 A | 4/1990 | Kopala et al. |
| 4,938,210 A | 7/1990 | Shene |
| 4,938,212 A | 7/1990 | Gnook et al. |
| 4,944,310 A | 7/1990 | Sullivan |
| D310,431 S | 9/1990 | Bellm |
| 4,960,121 A | 10/1990 | Nelson et al. |
| 4,971,051 A | 11/1990 | Toffolon |
| 4,986,269 A | 1/1991 | Hakkinen |
| 4,989,596 A | 2/1991 | Macris et al. |
| 4,989,599 A | 2/1991 | Carter |
| 5,005,568 A | 4/1991 | Loescher et al. |
| 5,005,571 A | 4/1991 | Dietz |
| 5,038,776 A | 8/1991 | Harrison et al. |
| 5,042,473 A | 8/1991 | Lewis |
| 5,042,478 A | 8/1991 | Kopala et al. |
| 5,046,200 A | 9/1991 | Feder |
| 5,063,922 A | 11/1991 | Hakkinen |
| 5,069,205 A | 12/1991 | Urso |
| 5,074,297 A | 12/1991 | Venegas |
| D323,908 S | 2/1992 | Hollister et al. |
| 5,086,768 A | 2/1992 | Niemeyer |
| 5,109,839 A | 5/1992 | Blasdell et al. |
| 5,109,840 A | 5/1992 | Daleiden |
| 5,121,745 A | 6/1992 | Israel |
| 5,133,347 A | 7/1992 | Huennebeck |
| 5,140,980 A | 8/1992 | Haughey et al. |
| 5,140,982 A | 8/1992 | Bauman |
| 5,159,938 A | 11/1992 | Laughlin |
| 5,178,138 A | 1/1993 | Walstrom et al. |
| 5,191,882 A | 3/1993 | Vogliano |
| D334,633 S | 4/1993 | Rudolph |
| 5,231,983 A | 8/1993 | Matson et al. |
| 5,233,978 A | 8/1993 | Callaway |
| 5,243,971 A | 9/1993 | Sullivan et al. |
| 5,260,015 A | 11/1993 | Kennedy et al. |
| 5,265,595 A | 11/1993 | Rudolph |
| 5,279,289 A | 1/1994 | Kirk |
| 5,280,784 A | 1/1994 | Kohler |
| 5,311,862 A | 5/1994 | Blasdell et al. |
| 5,322,057 A | 6/1994 | Raabe et al. |
| 5,343,878 A | 9/1994 | Scarberry et al. |
| 5,357,951 A | 10/1994 | Ratner |
| 5,372,130 A | 12/1994 | Stern et al. |
| 5,388,571 A | 2/1995 | Roberts et al. |
| 5,404,871 A | 4/1995 | Goodman et al. |
| 5,419,318 A | 5/1995 | Tayebi |
| 5,429,126 A | 7/1995 | Bracken |
| 5,429,683 A | 7/1995 | Le Mitouard |
| 5,431,158 A | 7/1995 | Tirotta |
| 5,438,981 A | 8/1995 | Starr et al. |
| 5,441,046 A | 8/1995 | Starr et al. |
| D362,061 S | 9/1995 | McGinnis et al. |
| 5,469,865 A | 11/1995 | Minneman |
| 5,477,852 A | 12/1995 | Landis et al. |
| 5,479,920 A | 1/1996 | Piper et al. |
| 5,488,948 A | 2/1996 | Dubruille et al. |
| 5,492,116 A | 2/1996 | Scarberry et al. |
| 5,501,214 A | 3/1996 | Sabo |
| 5,509,404 A | 4/1996 | Lloyd |
| 5,517,986 A | 5/1996 | Starr et al. |
| 5,518,795 A | 5/1996 | Kennedy et al. |
| 5,533,524 A | 7/1996 | Minneman |
| 5,538,000 A | 7/1996 | Rudolph |
| 5,540,223 A | 7/1996 | Starr et al. |
| 5,542,128 A | 8/1996 | Lomas |
| 5,546,936 A | 8/1996 | Virag et al. |
| 5,555,569 A | 9/1996 | Lane |
| 5,558,089 A | 9/1996 | Castigilone |
| RE35,339 E | 10/1996 | Rapoport |
| 5,560,354 A | 10/1996 | Berthon-Jones et al. |
| 5,570,682 A | 11/1996 | Johnson |
| 5,570,689 A | 11/1996 | Starr et al. |
| D377,089 S | 12/1996 | Starr et al. |
| 5,592,938 A | 1/1997 | Scarberry et al. |
| 5,608,647 A | 3/1997 | Rubsamen et al. |
| 5,642,730 A | 7/1997 | Baran |
| 5,647,355 A | 7/1997 | Starr et al. |

| | | | |
|---|---|---|---|
| 5,647,357 A | 7/1997 | Barnett et al. | |
| 5,649,532 A | 7/1997 | Griffiths | |
| 5,649,533 A | 7/1997 | Oren | |
| 5,655,520 A | 8/1997 | Howe et al. | |
| 5,655,527 A | 8/1997 | Scarberry et al. | |
| 5,657,493 A | 8/1997 | Ferrero et al. | |
| 5,657,752 A | 8/1997 | Landis et al. | |
| 5,662,101 A | 9/1997 | Ogden et al. | |
| 5,666,946 A | 9/1997 | Langenback | |
| 5,685,296 A | 11/1997 | Zdrojkowski et al. | |
| 5,687,715 A | 11/1997 | Landis et al. | |
| 5,715,814 A | 2/1998 | Ebers | |
| 5,744,080 A | 4/1998 | Kennedy et al. | |
| 5,763,041 A | 6/1998 | Leak et al. | |
| 5,921,239 A | 7/1999 | McCall et al. | |
| 6,044,844 A | 4/2000 | Kwok et al. | |
| 6,062,222 A | 5/2000 | Lewis et al. | |
| 6,174,476 B1 | 1/2001 | Kennedy et al. | |
| 6,248,419 B1 | 6/2001 | Kennedy et al. | |
| 6,412,487 B1 | 7/2002 | Gunaratnam et al. | |
| 6,467,482 B1 | 10/2002 | Boussignac | |
| 6,494,207 B1 | 12/2002 | Kwok | |
| 6,615,834 B2 * | 9/2003 | Gradon et al. | 128/207.11 |
| 6,631,718 B1 | 10/2003 | Lovell | |

FOREIGN PATENT DOCUMENTS

| | | |
|---|---|---|
| DE | 19962515 A1 | 7/2001 |
| EP | 0 234 746 A1 | 9/1987 |
| EP | 1020201 A2 | 7/2000 |
| GB | 826 198 A | 12/1959 |
| JP | 55-101142 | 7/1980 |
| JP | 64-32870 | 2/1989 |
| JP | 04-111356 | 9/1992 |
| JP | 2001-231860 | 8/2001 |
| JP | 2003/511160 | 3/2003 |
| JP | 2003/516825 | 5/2003 |
| WO | 98/48878 | 11/1998 |
| WO | WO 99/43375 A1 | 9/1999 |
| WO | 01/26722 A1 | 4/2001 |
| WO | 01/43804 A1 | 6/2001 |
| WO | WO 02/47749 A1 | 6/2002 |

OTHER PUBLICATIONS

Decision of Rejection issued in Japanese Appln. No. 2004-525073 (w/English translation), Apr. 6, 2010.
Supplementary European Search Report for corresponding EP Application No. 03766073, mailed Dec. 15, 2010, 5 pages.
Decision of Rejection issued in Japanese Appln. No. 2010-176666 (w/English translation), Nov. 24, 2010.
Office Action issued in a corresponding Japanese Appln. No. 2011-183841 (Dec. 11, 2012) with English translation thereof.
Office Action and English Translation for copending Japanese Application No. 2010-176666, mailed Apr. 26, 2011, 4 pages.

* cited by examiner

INEXTENSIBLE HEADGEAR AND CPAP OR VENTILATOR MASK ASSEMBLY WITH THE SAME

CROSS-REFERENCE TO RELATED APPLICATION

This application is a national phase under 35 U.S.C. 371 of PCT/AU2003/000988, filed Aug. 5, 2003, which claims the benefit of U.S. Provisional Application Ser. No. 60/400,686, filed Aug. 5, 2002, each of which is incorporated herein by reference in its entirety.

BACKGROUND OF THE INVENTION

1. Field of the Invention

This invention relates to a respiratory mask for use with a non-invasive positive pressure ventilation device and headgear for use with such a respiratory mask, and a frame to allow connection of a respiratory mask to the headgear.

2. General Background and Related Art

Non-invasive positive pressure ventilation (NIPPV) techniques, such as, for example, the application of continuous positive airway pressure (CPAP), have been used for the treatment of Sleep Disordered Breathing (SDB), such as Obstructive Sleep Apnea (OSA). An apparatus for applying NIPPV typically comprise a blower, an air delivery conduit, and a patient interface. A number of different patient interfaces are known, such as nasal masks, nose and mouth masks, full face masks, and nasal prongs or pillows. In all cases, some form of mask retaining feature, such as a headgear, is required to position the mask on the face and to counterbalance the force which results from the application of pressurized air that seeks to push the mask off the face.

A nasal mask typically comprises a generally triangularly shaped chamber constructed from a relatively rigid material, such as polycarbonate, with an open side that, when in use, is positioned against the face. The edge of the open side typically includes a cushion that helps form a seal on the patient's face. The cushion is typically soft to facilitate patient comfort. It is important that there be a good seal with few leaks because leaks can compromise therapy, e.g., cause air jetting and noise, which may be uncomfortable for the patient and cause improper functioning of the blower. Patient comfort is important since the patient must sleep while wearing the mask.

Prior art masks have typically been fairly uncomfortable for the patient. Previously, the masks themselves were uncomfortable due to a relatively small surface area (i.e., contacting area) of the cushion and an insubstantial degree of flexibility of the cushion. However, there have been advances in the design of masks, which have increased the surface area and the flexibility of the cushion. Therefore, the masks themselves have been improved in design so as to allow relatively comfortable engagement with the face. However, there remains a deficiency in the art to hold the mask to the patient's face in a manner that is comfortable for the patient for all pressures delivered to the mask.

In particular, previous designs of headgear that connect to the mask to hold the mask to the face, have utilized flexible straps which generally wrap around the head and connect to the mask (or a frame connected to the mask). The straps of the headgear are constructed of elastic, extensible material to increase patient comfort. However, the elasticity of the straps requires the mask to be strapped to the patient's face with an uncomfortable pressure. This is because the mask must be held to the face with strap tension sufficient to prevent leaks of air between the cushion and the face when the blower delivers a high pressure of air to the mask. The straps may be adjusted so that the residual elastic force in the straps is negligible to decrease the pressure applied to the face by the mask. However, this may be insufficient to hold the mask to the face during high pressure air delivery with sufficient force to prevent leaks. Even if no leaks are present, the mask may be caused to lift away from the face due to the high pressure of air, which reactively stretches the straps of the headgear. After lifting away, the elasticity of the straps causes the mask to recoil against the face upon cessation of the high pressure air delivery.

Stated differently, in the case of use with a varying air pressure source such as a ventilator or automatic CPAP device, or a CPAP device with an initial pressure ramp, if the straps are done up or tensioned sufficiently tight to seal at high pressure, there will be unnecessary excess force on the face at low pressure. Conversely, if the straps are done up or tensioned enough to just seal at low pressure, the mask will lift off the face and leak at high pressure.

Additionally, elastic straps of previous headgear designs have a tendency to wander or slide about the patient's head when the patient moves during sleep. This sliding of the headgear may cause headgear tension vectors to move away from their optimal position giving rise to leak and/or discomfort.

Furthermore, straps of prior art headgear have typically not been designed to allow both precise and easy adjustment. Therefore, the straps and adjustment of them were relatively cumbersome to the patient. Additionally, the elastic and pliable straps tend to flop and tangle when donning the headgear. Moreover, many designs required the patient to refit the headgear every time the headgear was removed and subsequently put back on.

Other drawbacks of the prior art relate to the connection of the headgear to the mask itself. This connection is accomplished either by clips attached directly to the mask and the straps of the headgear, or by use of a frame. Typical frames are connected to the mask and have connection points or clips thereon to allow connection of straps of the headgear. Typically, one or more connections of straps to the frame were of a quick release type to allow emergency removal of the mask. However, previous designs for frames have required additional componentry which increases costs of the mask/headgear assembly and/or have required some form of forehead support. Additional contact of the frame with the face may decrease the degree of comfort for the patient.

SUMMARY OF THE INVENTION

It is therefore one aspect of the invention to overcome the deficiencies noted above with respect to prior art masks and headgear.

It is another aspect to provide a headgear that provides a secure fit of a mask without compromising patient comfort and/or the seal between the cushion and the patient.

It is yet another aspect to provide a headgear that provides a secure fit of a mask and is relatively easy to adjust.

It is a further aspect of the invention to provide headgear that retains its shape, like a cap.

It is a further aspect of the invention to provide headgear which allows for microadjustment of headgear tension.

It is a further aspect of the invention to provide a mask frame which is selectively deformable.

It is a further aspect of the invention to provide a mask frame which is micro-deformable.

It is a further aspect of the invention to provide a mask cushion which is controllably inflatable.

In accordance with one embodiment of the invention, a respiratory mask for a CPAP device is provided. The headgear includes a strap portion formed of a substantially inextensible material. The strap portion has formed on one end thereof a connecting structure configured to connect to a respiratory mask.

In accordance with another embodiment of the invention, a headgear is provided for a respiratory mask of a ventilator or CPAP device. The headgear includes a strap portion formed of a substantially inextensible material and having formed on one end thereof a connecting structure that is configured to adjustably connect to the mask so as to allow a spacing between the strap and mask to be altered.

These and other aspects will be described in or apparent from the following detailed description of preferred embodiments.

DETAILED DESCRIPTION OF PREFERRED EMBODIMENTS

"Omega" Nose and Mouth Mask

Figure 1:
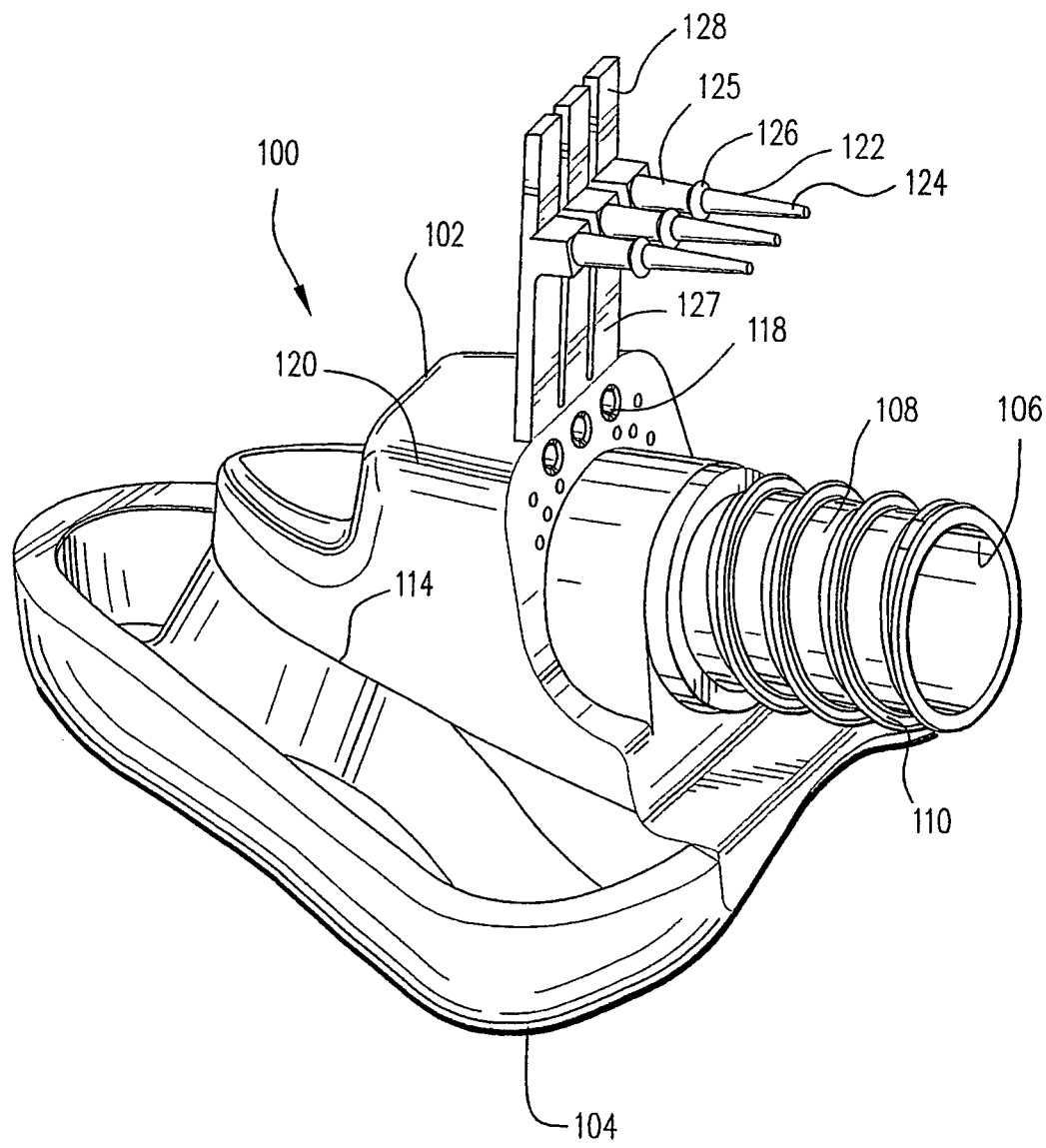
FIG. 1 is a perspective view of a respiratory mask according to one embodiment of the invention.
Figure 2:
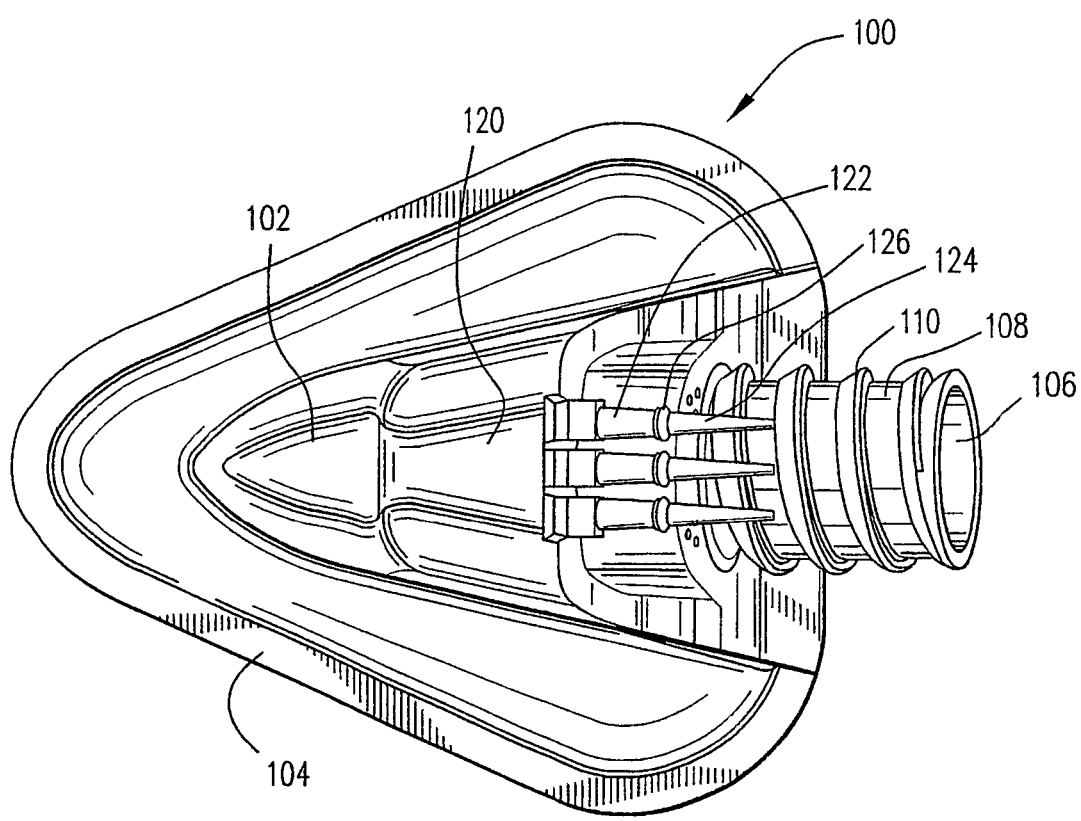
FIG. 2 is a top plan view of the respiratory mask shown in FIG. 1.
Figure 3:
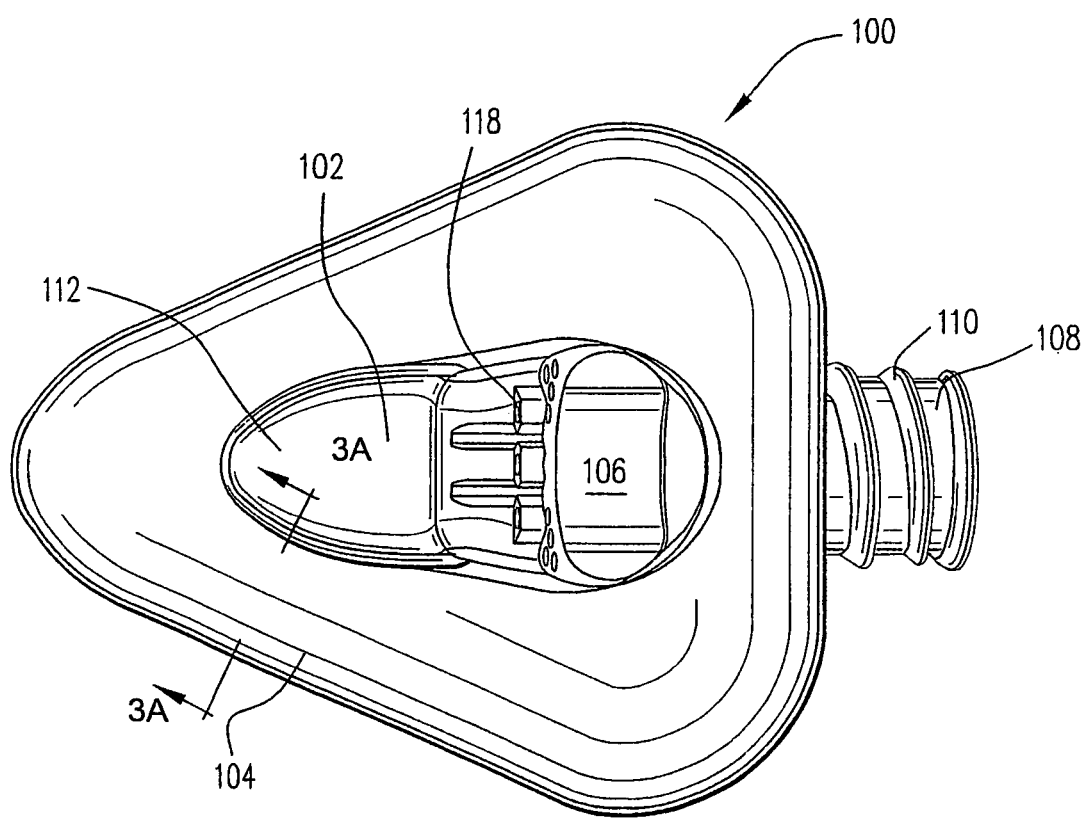
FIG. 3 is a bottom plan view of the respiratory mask shown in FIG. 1.

FIG. 1 shows a respiratory mask, generally indicated at 100, embodying the principles of one embodiment of the present invention. As shown, the mask 100 includes a shell structure 102 and a cushion 104. It is noted that the mask 100 is shown as a type configured to fit around both a nose and mouth of a patient. It is also contemplated, however, that the mask 100 may be of a type to fit around just the nose or just the mouth of the patient without diverting from the principles of the invention. Accordingly, the mask 100 and, in particular, the cushion 104 has a general triangular shape, as can be seen in FIGS. 2 and 3. In one form, a face-contacting portion of the cushion 104 comprises a compliant foam structure having an external air-tight skin. The skin could be a separate molding or an integral skinned foam. Where the skin is separate, the skin could be attached at peripheral points to the foam. Alternatively, the skin could be attached to the foam using an adhesive. Materials suitable for forming either the foam or the skin include polyurethane and silicone.

The shell structure 102 has a substantially hollow, or cup-like, configuration, as shown in FIG. 3. The shell structure 102 has an inlet 106 connected thereto, which is defined by a substantially cylindrical tube portion 108, which extends from the shell structure 102. The tube portion 108 is configured to engage and communicate with a ventilation conduit (not shown), which ventilation conduit is communicated to a ventilator or a continuous positive airway pressure (CPAP) device of the type to supply a breathable gas above atmospheric pressure to the shell structure 102. The tube portion 108 includes a series of rib structures 110 on an outer periphery thereof. It is contemplated that the rib structures 110 may be arranged in a helical configuration, such as shown in FIG. 2. The rib structures 110 provide a relative rigidity to the tube portion 108 so as to prevent collapse of the tube portion 108. Accordingly, the CPAP device may supply breathable gas above atmospheric pressure to an inner periphery 112 of the shell structure 102 for inhalation by the patient.

Figure 3A:
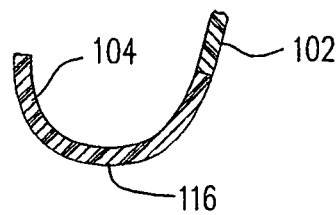
FIG. 3A is a cross sectional view of the respiratory mask shown in FIG. 3 taken along line I-I.

As shown in FIG. 1, the shell structure 102 includes a peripheral portion 114 attached to the cushion 104. The cushion 104 is preferably formed of a substantially pliable or flexible (and also preferably soft) material, such as silicone. As shown in FIG. 3A, the cushion 104 has a generally U-shaped configuration so as to provide a broad face contacting surface 116. It is contemplated that the cushion 104 may be connected to the peripheral portion 114 of the shell structure 102 by use, for example, of adhesives, or may be formed integrally with the shell structure 102.

Port Caps

Referring back to FIG. 1, the shell structure 102 also includes at least one auxiliary port 118 extending through a crest portion 120 of the shell structure 102. The auxiliary port 118 is communicated with the inner periphery 112 of the shell structure 102 and is preferably configured to allow connection of, e.g., monitoring devices, an alarm, and/or an auxiliary fluid delivery conduit (e.g., an oxygen delivery tube). As shown in FIG. 1, the shell structure 102 includes three (3) auxiliary ports 118, however, there may be any number of auxiliary ports provided. The auxiliary ports 118 allow certain monitoring devices (not shown) to be connected thereto so as to monitor, for example, pressure within the inner periphery 112 of the shell structure 102 or noise produced by the patient's breathing (e.g., snoring).

Figure 4:
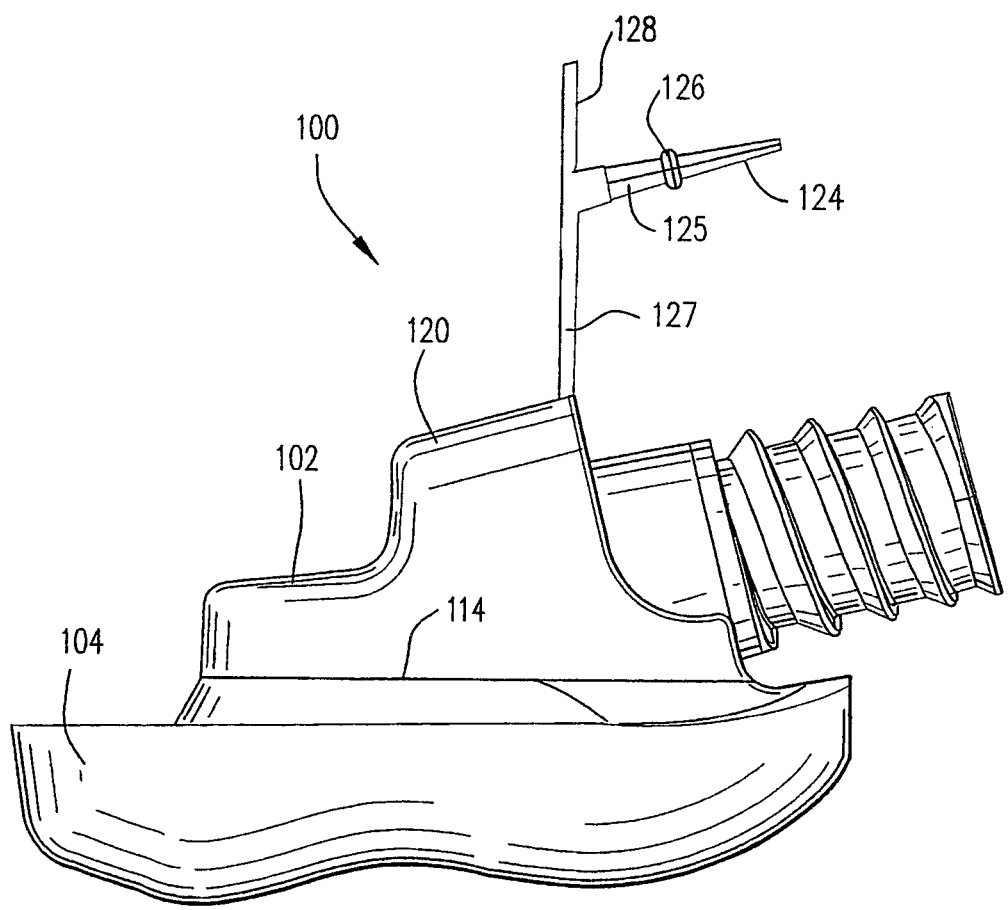
FIG. 4 is a side view of the respiratory mask shown in FIG. 1.

As shown in FIGS. 1 and 4, the shell structure 102 also provides a port cap 122 thereon. The port cap 122 is used to "plug" the auxiliary port 118, such as when the auxiliary port 118 is not needed. In this manner, in cases when the auxiliary port 118 is not needed, the port cap 122 may be inserted therein to substantially prevent leakage of air and noise created by air flowing therethrough. The port cap 122 includes a tapered portion 124 to facilitate the insertion of the port cap 122 within the auxiliary port 118 and an annular enlarged cap portion 125 that is configured to relatively snugly fit within the auxiliary port 118 to engage an interior of the port 118 and thereby prevent air leakage. Retaining ring 126 mitigates inadvertent removal of the cap 125.

FIGS. 1 and 4 also show an extending member 127 extending outwardly from the shell structure 102 and providing an attachment for the port cap 122. Removal tab 128 provides means for the user to pull open the port cap 122. It is preferable that the port cap 122, the extending member 127 and the removal tab 128 are formed integrally (e.g., as one piece) together. In fact, it may be preferable for the shell structure 102, the extending member 127, the removal tab 128 and the port cap 122 to be formed integrally together. In this manner, these separate components may be formed in a single manufacturing process, such as a molding process. For example, the shell structure 102, the extending member 127, the removal tab 128 and the port cap 122 may be formed by injection molding. Due to the integral nature of these components, they may be formed such as by injection molding with only one shot needed to form all of them.

FIG. 1 shows the shell structure 102 formed with three (3) extending members 127 and three (3) port caps 122 corresponding to the three (3) auxiliary ports 118. It is preferable that the extending member 127 be formed of a material with sufficient flexibility to allow the port cap 122 to be moved into position relative to the auxiliary port 118 and to be inserted therein. Accordingly, the extending member 128 is preferably capable of bending into a substantially U-shaped orientation. This arrangement is advantageous, as it is relatively simple to manufacture, reduces componentry, and reduces the tendency of the port caps 122 to be misplaced.

Headgear that Retains its Shape

Figure 5:
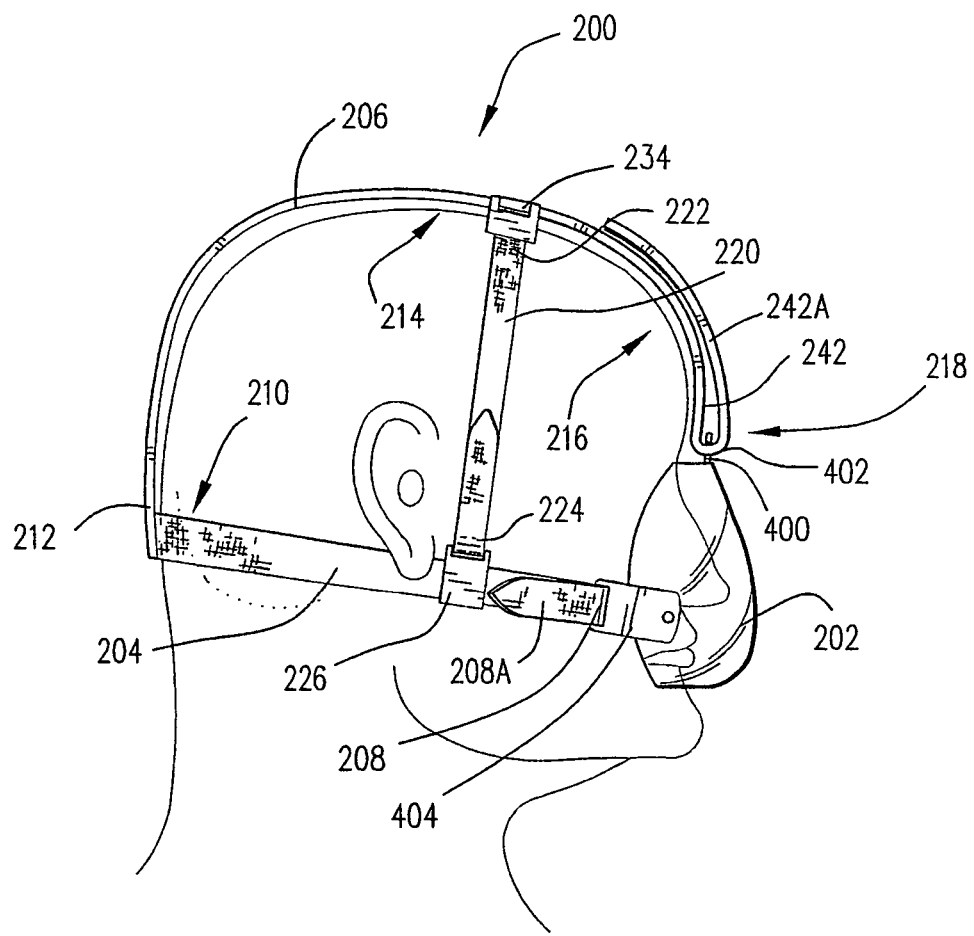
FIG. 5 is a side view of a headgear according to one embodiment of the invention shown in position on a patient's head.
Figure 6:
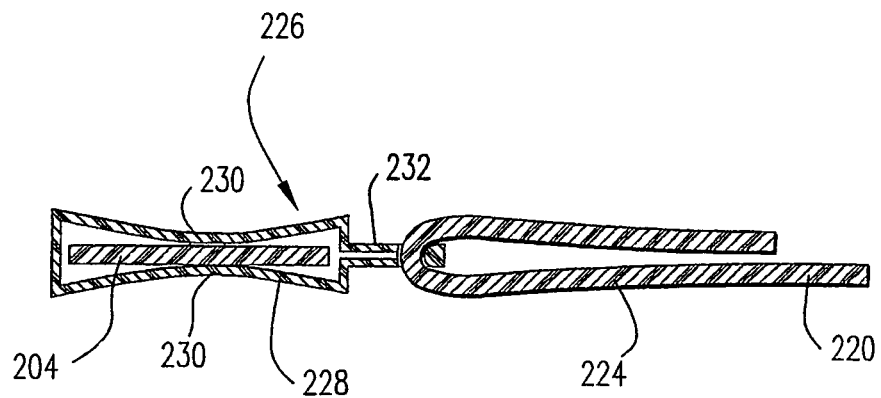
FIG. 6 is a cross-sectional view of a clip element in use with the headgear shown in FIG. 5.
Figure 7:
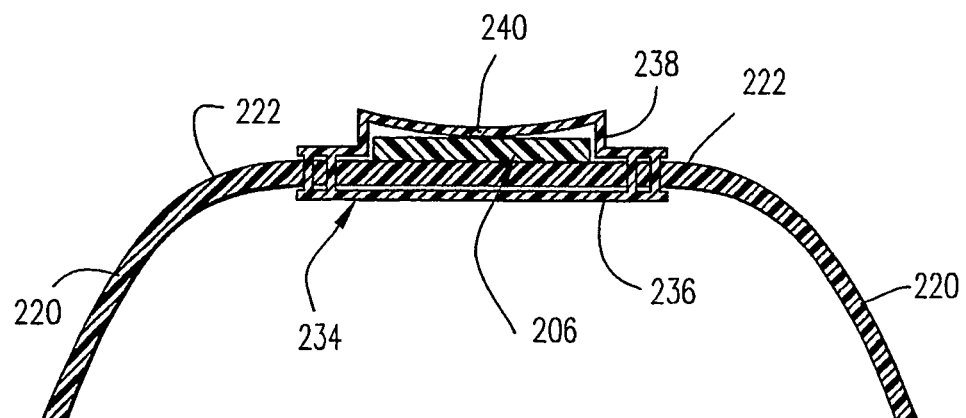
FIG. 7 is a cross-sectional view of another clip element in use with the headgear shown in FIG. 5.

FIGS. 5-7 show one embodiment of a headgear, indicated at 200, which may be used with the mask 100 previously described. As shown, the headgear 200 includes a plurality of straps that are configured and arranged so as to substantially surround the patient's head and are connected to a mask 202 to thereby retain the mask 202 in relation to the patient's face. It is noted that the mask 202 is shown merely as an example to demonstrate the application of the headgear 200 and that the mask 100 previously described, or any other suitable respiratory mask, may be alternatively used. To retain the mask 202 in position, the headgear 200 utilizes a horizontal strap 204 and a sagittal strap 206. The horizontal strap 204 is arranged generally horizontally and wraps circumferentially around the patient's head. Each end 208 of the horizontal strap 204 is coupled to the mask 202. The specific connection between the horizontal strap 204 and mask 202 will be discussed in further detail below. The horizontal strap 204 is preferably arranged to pass just inferiorly to each ear and across the insertion area of the neck muscles into the base of the skull which is generally indicated at 210 in FIG. 5.

A posterior end 212 of the sagittal strap 206 is connected generally at a mid-point of the horizontal strap 204 so as to be positioned at an immediate posterior area of the patient's head. The sagittal strap 206 extends from the horizontal strap 204 (i.e., the posterior end 212), across the vertex of the scull, generally indicated at 214, extends generally anteriorly across a forehead of the patient's head, generally indicated at 216, and has a anterior end 218 coupled to the mask 202. It may also be preferable for the headgear 200 to include a pair of coronal straps 220 that interconnect the horizontal and sagittal straps 204, 206. A superior end 222 of each coronal strap is connected to the sagittal strap proximate the vertex 214 of the patient's head. Each coronal strap extends from the vertex 214 (i.e., the superior end 222) laterally and anteriorly across the head and connects to the horizontal strap 204 just anteriorly to and just inferiorly to each ear at inferior ends 224 of the coronal straps 220.

Each inferior end 224 of the coronal straps 220 is connected to the horizontal strap 204 via a clip element 226. As shown in FIG. 6, each clip element 226 includes a sliding portion 228 within which the horizontal strap 204 is disposed. In this manner, the clip element 226 may be adjustably moved posteriorly or anteriorly along the horizontal strap 204. In order to retain the clip element 226 in position relative to the horizontal strap 204, the sliding portion 228 is configured with opposing detent portions 230. The detent portions 230 engage the horizontal strap 204 at opposites sides thereof (i.e., exterior and interior side thereof, relative to the patient's head) to thereby prevent movement of the clip element 226 and therefore the inferior end 224 of the coronal strap 220 relative to the horizontal strap 204. Each clip element 226 also includes a loop structure 232 within which the inferior and 224 of the coronal 220 passes. Accordingly, the inferior end 224 may be secured from sliding within the loop structure 232 by, for example, hook and loop mating tapes (e.g., Velcro) or other suitable connecting arrangements.

Referring back to FIG. 5, another clip element 234 is used to connect each superior end 222 of the coronal straps 220 to the sagittal strap 206. The clip element 234 is shown in greater detail in FIG. 7. It is contemplated that the coronal straps 220 may be formed by a singular strap, such as shown in FIG. 7. The clip element 234 includes a coronal strap receiving portion 236 within which the coronal strap 220 is disposed. Additionally, the clip element 234 includes a sliding portion 238 within which the sagittal strap 206 is disposed. The sliding portion 238 includes a detent portion 240, which engages the sagittal strap 206 to thereby retain the sagittal strap 206 and coronal strap 220 in relative positions. However, due to the slidable nature of the connections between the sagittal strap 206 and coronal straps 220 and the clip element 234, adjustment of the coronal straps 220 relative to the sagittal strap 206 is possible.

Figure 8:
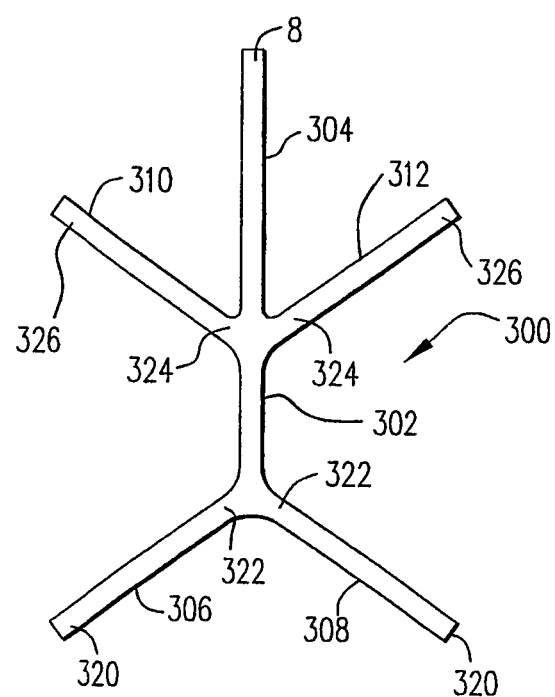
FIG. 8 is a top plan view of a headgear according to another embodiment of the invention.
Figure 9:
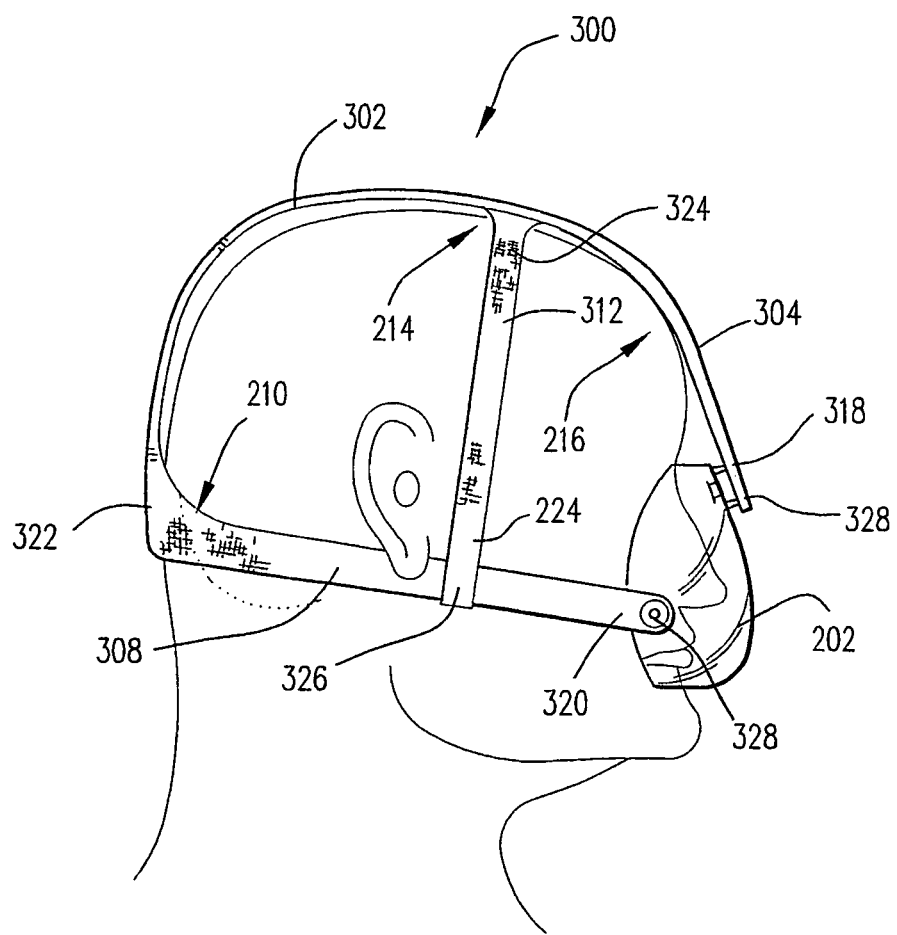
FIG. 9 is a side view of the headgear shown in FIG. 8 in position on a patient's head.

As shown in FIGS. 8 and 9, it is possible that a headgear 300, which is similar to that shown in FIG. 5, may be formed from a singular piece of material. As shown, the headgear 300 includes first and second sagittal strap portions 302, 304. The first sagittal strap portion 302 is similar to sagittal strap 206, in that strap 302 extends across the vertex 214 of the patient's head. The second sagittal strap portion 304 extends across the forehead 216 and connects to the mask 202 at an anterior end 318 thereof. The headgear 300 also includes first and second horizontal strap portions 306, 308. Each horizontal strap portion 306, 308 wraps partially circumferentially about the patient's head and is positioned just inferiorly to the patient's ear. Anterior ends 320 of the horizontal strap portions 306, 308 are releasably connected to the mask 202. Posterior ends 322 of the horizontal strap portions 306, 308 intersect with the sagittal strap portion 302 proximate the insertion area 210 of the neck muscles into the base of the skull. Additionally, the headgear 300 includes first and second coronal strap portions 310, 312. The coronal strap portions 310, 312 have superior ends 324 thereof that intersect the first and second sagittal strap portion 302, 304 and extend therefrom proximate the vertex 214 laterally and anteriorly across the head and connects to respective horizontal strap portions 306, 308 just anteriorly to and just inferiorly to respective ears at inferior ends 326 thereof.

It is contemplated that the headgear 300 may be formed from a singular piece of material, such as stamped from a piece of sheet material. It is noted, however, that a degree of adjustability, as described for the embodiment shown in FIG. 5, will be compromised due to the integral and non-adjustable relation of the strap portions.

It is noted that in order to maintain a secure and comfortable fit of the mask 200, the straps of the headgear 200, 300 are preferably formed to be substantially inextensible. In other words, the straps may be somewhat flexible, however, are preferably not capable of significant elongation. The straps have sufficient stiffness or rigidity to retain their shape. Contemplative materials for the straps include polyvinyl chloride (PVC), leather, polypropylene, or polyurethane. Other materials are, of course, possible. For example, another contemplated suitable material may be a relatively strong cloth tape. It is also contemplated that the straps may be lined with a felt material to add to a degree of comfort to the patient. Other alterations may include perforations or holes to allow cooling through the straps.

Connecting Mask to Headgear

As discussed previously, the headgear 200, 300 is coupled to the mask 202 and, preferably, in a manner so as to allow adjustment of the position of the mask 202 relative to the straps of the headgear 200, 300. FIG. 5 shows two contemplated arrangements for connecting straps to the mask 202. The first includes a flange structure 400 extending from the mask 202. As shown, an anterior portion 242 of the sagittal strap 206 passes through a receiving aperture 402 within the flange structure 400. A tail portion 242A of the sagittal strap 206 may then be folded back over the anterior portion 242. The tail portion 242A may then be secured to the anterior portion 242 by use of, for example, hook and loop mating tapes (e.g., Velcro), snap elements, or rivet-type connectors. It may, however, be preferable to secure the tail portion 242A of the sagittal strap 206 in a manner that would allow subsequent readjustment of the strap 206.

Figure 10:
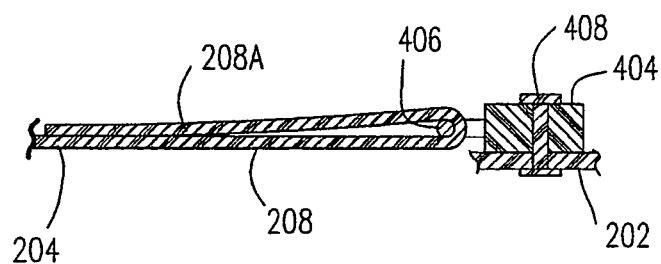
FIG. 10 is a cross-sectional view of a connecting structure used to connect the headgear shown in FIG. 8 with a mask.

The second attachment arrangement shown in FIG. 5 is shown connecting the end 208 of the horizontal strap 204 to the mask 202. Specifically, the end 208 is attached to a connecting structure 404, which itself is connected to the mask 202. As shown in FIG. 10, the connecting structure 404 may include a flange structure 406 through which the anterior end 208 of the horizontal strap 204 passes. A tail portion 208A of the horizontal strap 204 is secured to the end 208 by, for example, hook and loop tape (e.g., Velcro), or other suitable fasteners. Additionally, the connecting structure 404 may be secured to the mask 202 by use of a mechanical fastener 408, which may be a rivet structure or press stud element.

Figure 11:
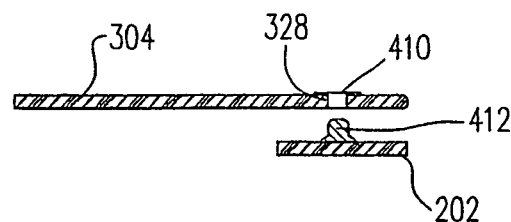
FIG. 11 is a cross-sectional view of another connection arrangement used to connect the headgear shown in FIG. 8 with a mask.

FIG. 9 shows another contemplated arrangement for connecting the headgear 200, 300 to the mask 202. This arrangement is shown with relation to headgear 300. As shown in FIG. 9, each anterior end 320 of each of the first and second horizontal strap portions 306, 308 and the anterior end 318 of the second sagittal strap portion 304 are provided with openings 328 therethrough. The formation of the openings 328 will be described in greater detail below. Referring to FIG. 11, within each of the openings 328, a female connecting element 410 is securely fastened, such as with a press-fit engagement. Additionally, the mask 202 is provided with three (3) male connecting elements 412, which releasably engage within respective female connecting elements 410 to secure each of the straps 304, 306, 308 to the mask 202. Accordingly, precise positioning of the female connecting elements 410 is preferable in order to provide a comfortable fit for the patient.

Figure 12:
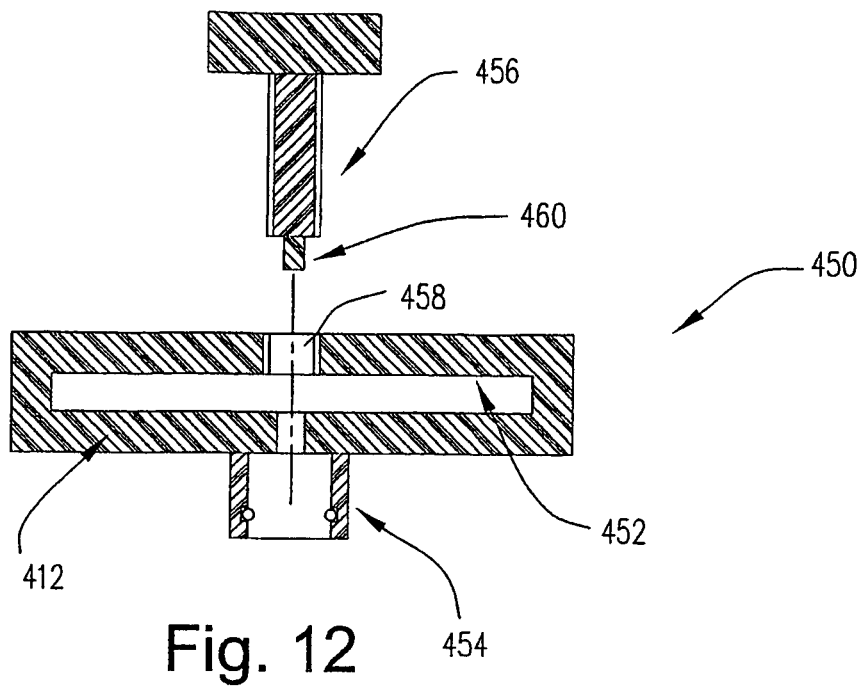
FIG. 12 is a cross-sectional view of a jig structure used to punch holes within straps of a headgear.

A preferred method of forming and positioning the openings 328 is now discussed with reference to FIG. 12. As shown, a fitting jig 450 is used to facilitate precise positioning of the female connecting elements 410. The fitting jig 450 has a slot 452 formed therein which receives the sagittal strap 304 one of the horizontal straps 306, 308. The fitting jig 450 also includes a female connecting portion 454, which is engaged with the corresponding male connecting element 412 on the mask 202, once the respective strap is inserted within the slot 452. The patient then dons the headgear and mask, while the fitting jigs 450 are in place on the straps. The straps are then adjusted by sliding within the slots 452 until a comfortable fit is reached. At this point, a punching element 456 is inserted within an aperture 458 within the fitting jig 450. A punch structure 460 on an end of the punching element 456 then engages the strap and may be pushed through the strap so as to punch an opening within the strap. Once the opening in the strap is formed, the fitting jig 450 may be removed from the strap, and a female connecting element 410 may then be inserted within the opening in the strap. The female connecting elements 410 are then located precisely to provide a comfortable fit.

Frame

Figure 13:
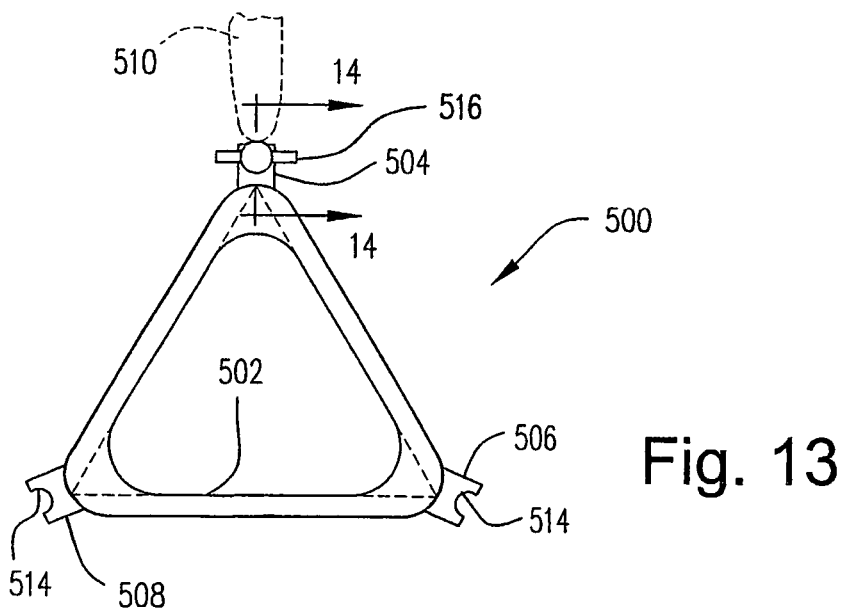
FIG. 13 is a top plan view of a frame according to another embodiment of the invention.

It is also contemplated that a frame 500 may be used to facilitate the connection of a respiratory mask with a headgear. As shown in FIG. 13, the frame 500 may be substantially triangular in shape and have a central opening 502 formed therein. It may be preferable for the frame 500 to be formed of a relatively thin metallic material, such as brass. The frame 500 includes three (3) outwardly extending connecting members 504, 506, 508, which are located at the respective points of the triangular configuration of the frame 500. It is contemplated that the frame 500 may be attached to a respiratory mask, such as the mask 100 shown in FIG. 1, by, for example, adhesives. It may, however, be preferable for a portion of the mask (such as the shell structure 102 of the mask 100) to be over-molded on the frame 500 in such a way that the frame 500 is substantially or partially encapsulated within the material of the mask, while the connecting members 504, 506, 508 are externally exposed.

Figure 14:
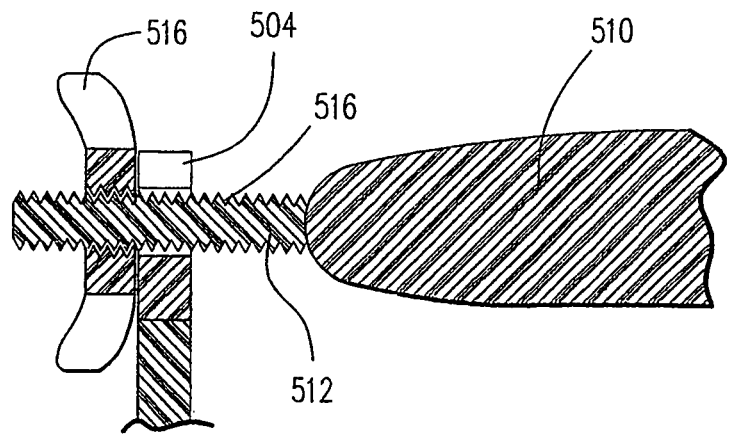
FIG. 14 is a cross-sectional view of a portion of the frame shown in FIG. 13 along line 14-14 in FIG. 13.

As shown in FIG. 14, each strap 510 of a headgear for use with the frame 500 preferably includes a terminal threaded member 512. As shown in FIG. 13, each of the connecting members 504, 506, 508 includes a substantially circular aperture 514. Referring back to FIG. 14, the threaded member 512 of the strap 510 is inserted within the corresponding aperture 514 and a threaded fastener 516 is threadedly engaged with the threaded member 512 of the strap 510. In this manner, the strap 510 is held relatively securely relative to the frame 500 and easy adjustment of the strap 510 is possible by rotation of the threaded fastener 516.

Alternative Headgear

Figure 15:
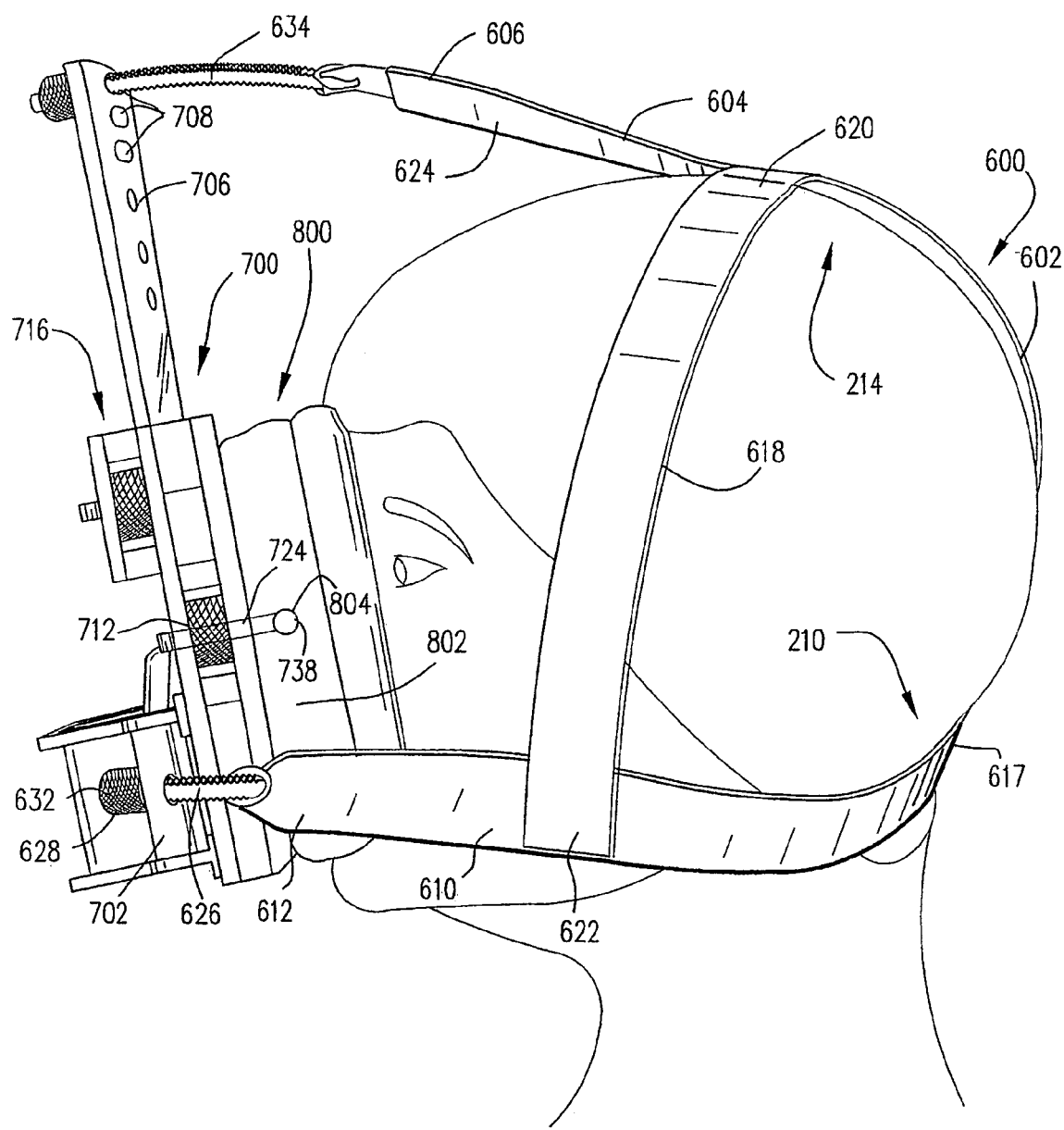
FIG. 15 is a side view of a headgear, frame, and mask according to another embodiment of the invention in position of a patient's head.
Figure 16:
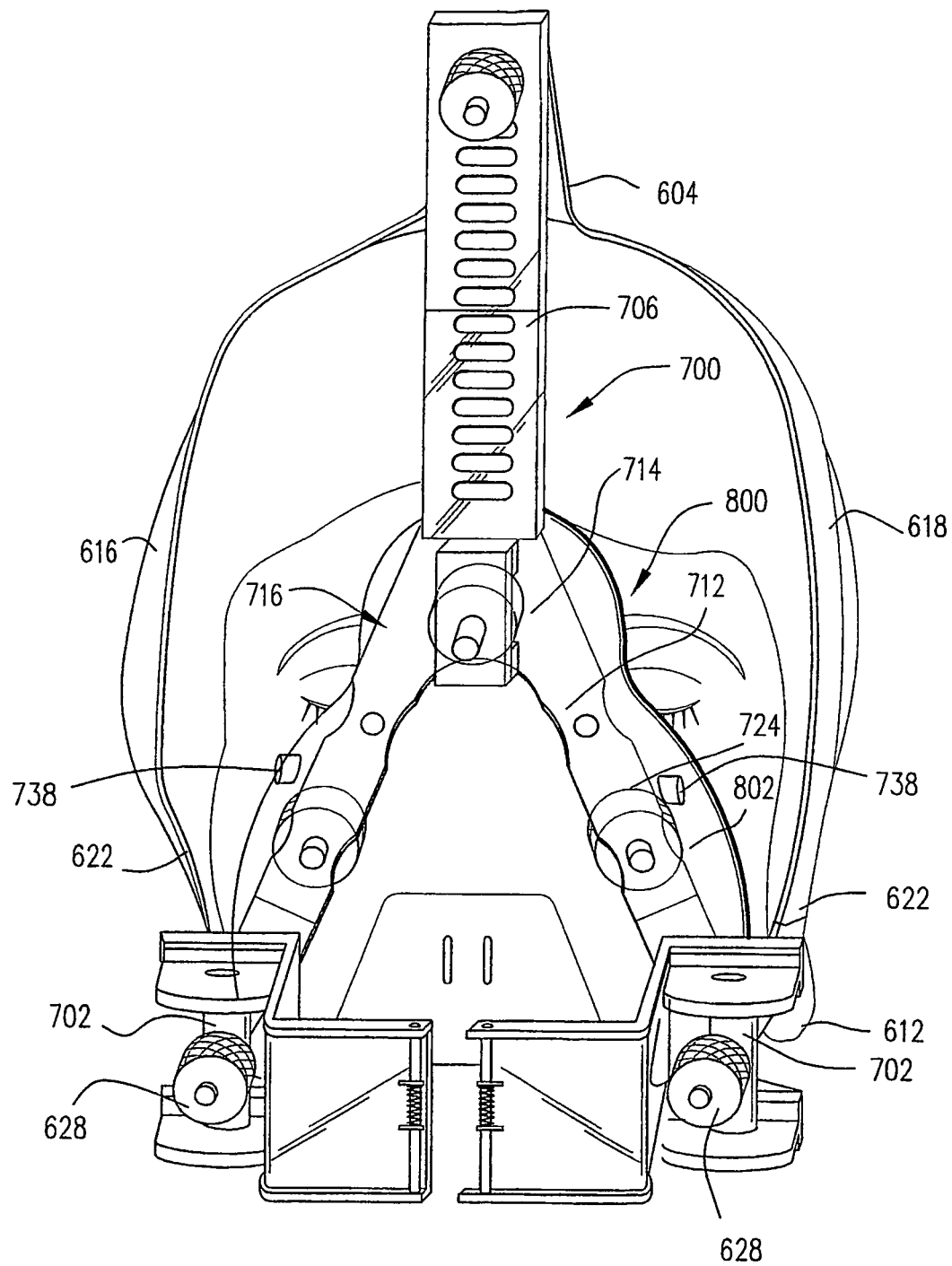
FIG. 16 is a front view of the headgear, frame, and mask shown in FIG. 15.

FIGS. 15 and 16 show other alternate embodiments of a headgear 600, a frame 700, and a mask 800. The headgear 600 includes first and second sagittal strap portions 602, 604. The first sagittal strap portion 602 extends across the vertex 214 of the patient's head. The second sagittal strap portion 604 extends from the first sagittal strap portion 602 proximate the vertex 214 in an anterior direction to connect with the frame 700 at an anterior end 606 thereof. The headgear 600 also includes first and second horizontal strap portions 608, 610. Each horizontal strap portion 608, 610 wraps partially circumferentially about the patient's head and is positioned just inferiorly to the patient's ear. Anterior ends 612 of the horizontal strap portions 608, 610 are adjustably connected to the mask 800, as will be discussed below. Posterior ends 614 of the horizontal strap portion 608, 610 intersect with the sagittal strap portion 602 proximate the insertion area 210 of the neck muscles into the base of the skull. Additionally, the headgear 600 includes first and second coronal strap portions 616, 618. The coronal strap portions 616, 618 have superior ends 620 thereof that intersect the first and second sagittal strap portions 602, 604 and extend therefrom proximate the vertex 214 laterally and anteriorly across the head and connect to respective horizontal strap portions 608, 610 just anteriorly to and just inferiorly to respective ears at inferior ends 622 thereof.

It is contemplated that the headgear 600 may be formed from a singular piece of material, such as stamped from a piece of sheet material. To maintain a secure and comfortable fit of the mask 800, the straps of the headgear 600 are preferably formed to be substantially inextensible. Preferably, the straps are somewhat flexible but are incapable of significant elastic elongation. The headgear has sufficient stiffness or rigidity to retain its shape. In this manner, the headgear 600 retains its shape and fit when not positioned on a patient's head and eliminates the necessity of manipulating floppy straps to don or remove the headgear, as in prior art headgear designs. Possible materials for construction of the headgear 600 include PVC, leather, polypropylene, and polyurethane. Other materials are, of course, possible. Other suitable materials include relatively strong cloth tapes. It is also contemplated that the straps may be lined with a relatively softer material, such as felt, as shown at 624 in FIG. 15. For example, a felt sheet material may be cut simultaneously with the straps of the headgear 600 and then subsequently fastened onto interior sides of the straps with, e.g., adhesives.

Microadjustment of Headgear with Fasteners

Figure 17:
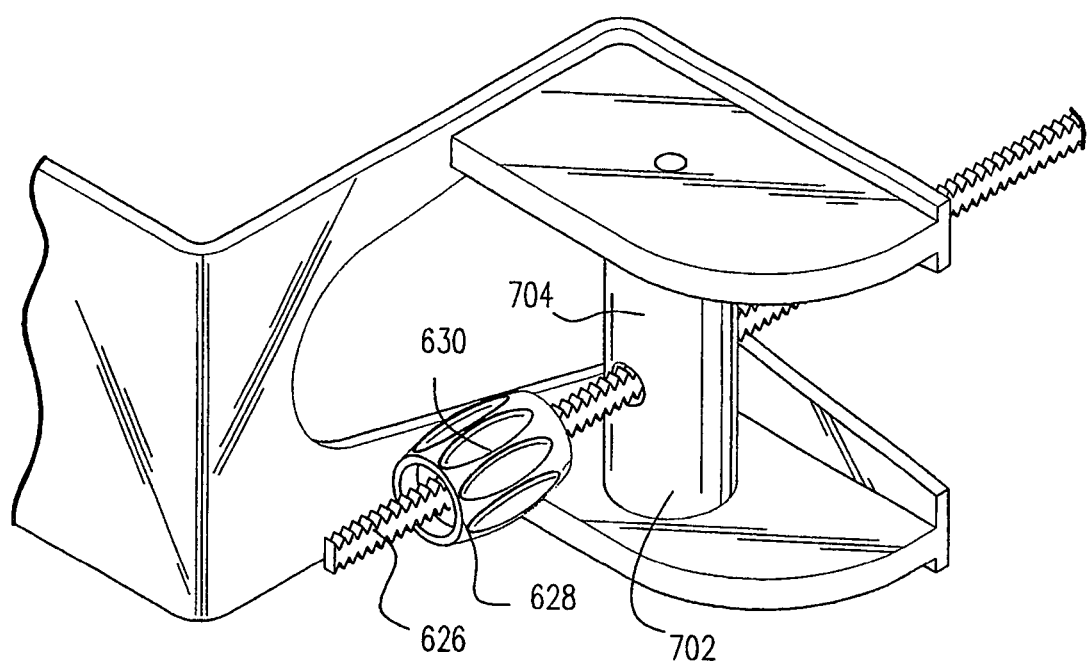
FIG. 17 is a perspective view of a connecting portion and fastener according to one embodiment of the invention.

The anterior ends 612 of the first and second horizontal strap portions 608, 610 are adjustably connected to the frame 700, as shown in FIGS. 15 and 16. Referring to FIG. 15, each anterior end 612 has attached thereto a threaded adjusting member 626 that is coupled to a connecting portion 702 of the frame 700. The threaded adjusting members 626 may be connected to the anterior ends 612 by, e.g., adhesive, fasteners (such as rivets), sewing, polymer welding, etc. It is also possible for the members 626 to be integrally formed with the straps themselves. As shown in greater detail in FIG. 17, the threaded adjusting member 626 extends through an opening (not shown) within the connecting portions 702. Preferably, the threaded adjusting member 626 has a non-circular cross-sectional configuration, such as a rectangular cross-sectional configuration as shown in FIG. 17. To prevent relative rotation between the threaded adjusting member 626 and connecting portions 702, the opening formed in each connecting portion 702 preferably has a cross-sectional configuration cooperable with the threaded adjusting member 626 so as to slidably and non-rotatably receive the threaded adjusting member 626 therein. A threaded fastener 628 is threadedly engaged with the threaded adjusting member 626 and abuts an anteriorly facing surface 704 of the connecting portion 702. Referring back to FIG. 15, a position of the frame 700 relative to the patient's head may be adjusted by advancing or retreating the threaded fastener 628 along the threaded adjusting member 626. Additionally, a tension present within the horizontal strap portions 608, 610 (and the other strap portions 602, 604, 616, 618) may also be varied by adjusting the position of the threaded fastener 628 relative to the threaded adjusting member 626.

It is contemplated that to ease manipulation of the threaded fasteners 628, especially for one-handed operation, the threaded fasteners 628 may have gripping features, such as circumferentially-spaced detents 630 shown in FIG. 17 or a knurled outer surface 632 as shown in FIG. 15.

Figure 18:
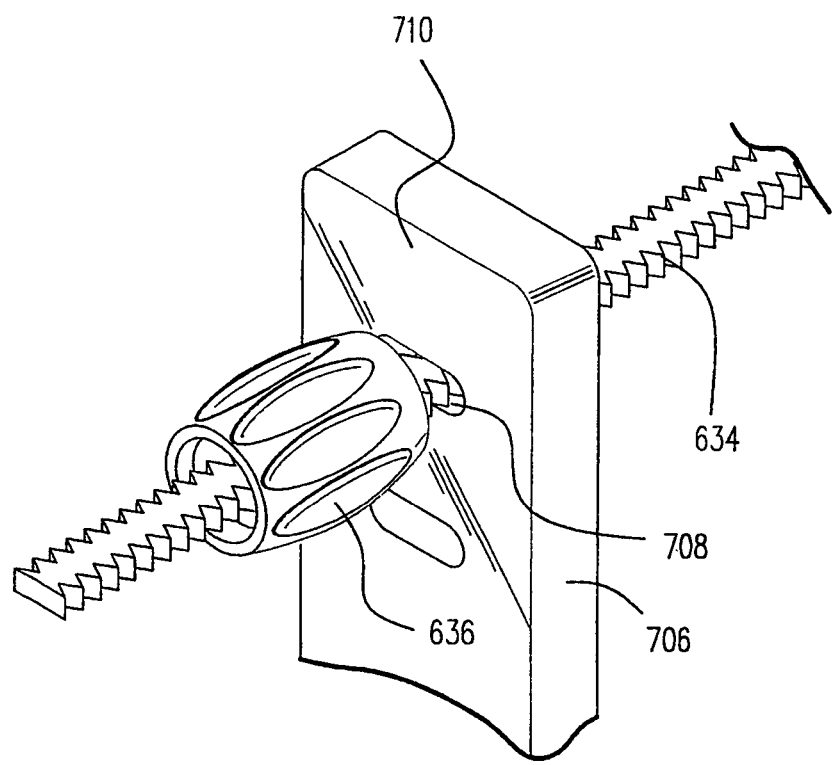
FIG. 18 is a perspective view of a connecting portion and fastener according another embodiment of the invention.

Referring back to FIG. 15, the anterior end 606 of the second sagittal strap portion 604 has connected thereto another threaded adjusting member 634. As with the threaded adjusting members 626, the threaded adjusting members 634 may be connected to the anterior end 606 of the sagittal strap portion 604 by, e.g., adhesive, fasteners, sewing, welding, or the like. It is also contemplated that the threaded adjusting member 634 may be integrally formed with the strap portion 604. The threaded adjusting member 634 extends anteriorly from the anterior end 606 and is adjustably coupled to the frame 700. In particular, the frame 700 includes a generally upwardly extending connecting portion 706 having formed therein one or more openings 708 within one of which the threaded adjusting member 634 extends. Referring to FIG. 18, the threaded adjusting member 634 has a non-circular cross-sectional configuration, such as rectangular. The opening 708 is preferably formed with a configuration cooperable with that of the threaded adjusting member 634 so as to slidably and non-rotatably receive the threaded adjusting member 634 therein. A threaded fastener 636 is threadedly engaged with the threaded adjusting member 634 and abuts an anteriorly facing surface 710 of the connecting portion 706. A position of the frame 700 relative to the patient's head, as well as a tension within the sagittal strap portion 604 (and the other strap portions 608, 610, 616, 618) may be adjusted by correspondingly advancing or retreating the threaded fastener 636 along the threaded adjusting member 634.

Referring back to FIG. 16, the frame 700 includes a generally triangular frame structure 712. The frame structure 712 has mounted thereto the mask 800. The connection therebetween will be discussed is greater detail below. The connecting portion 706 is connected to the frame 712 at an upper vertex 714 of the triangular frame 712. A screw mechanism 716 may allow adjustment of the horizontal position of the connecting portion 706 relative to the frame 712. It is also contemplated that a vertical position of the sagittal strap portion 604 may be adjusted relative to the connecting portion 706 by locating the threaded adjusting member 634 in a lower or higher opening 708.

Quick Release

Figure 19:
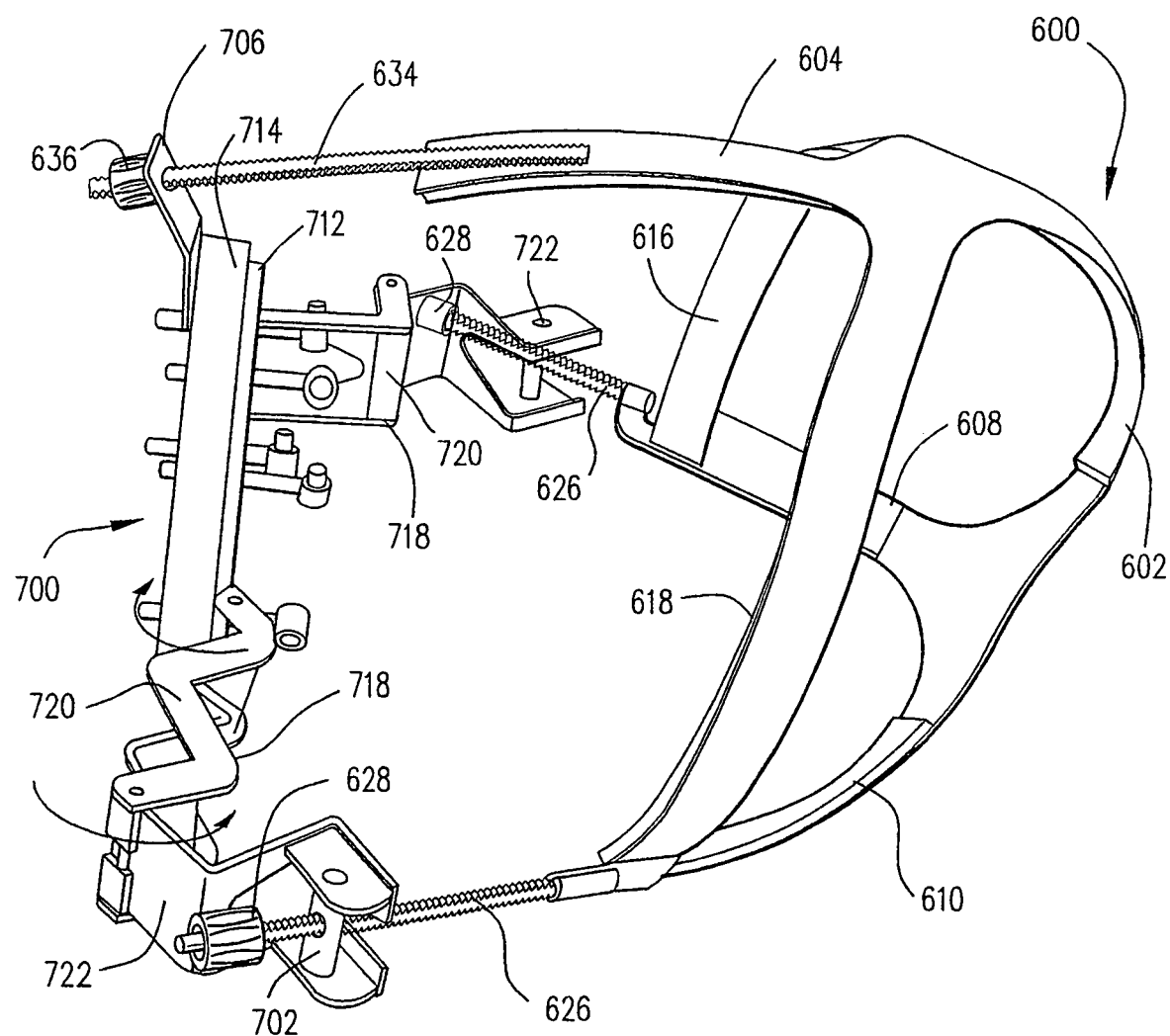
FIG. 19 is a perspective view of the headgear, frame, and mask shown in FIG. 15 in a released position.

It is contemplated that the frame 700 may include a pair of horizontally opposing connecting arms 718, such as shown in FIG. 19. Each connecting arm 718 includes first and second arm portions 720, 722. Inner ends of the first arm portions 720 are pivotably connected to the frame 712 at opposing horizontally spaced vertices of the frame 712 and outer ends of the first arm portion 720 are pivotally connected to inner ends of the second arm portions 722. Outer end portions of the second arm portion 722 provide the connecting portions 702 thereon.

The connecting arms 718 are configured to provide a quick release mechanism to allow the patient to easily remove the headgear 600, frame 700, and mask 800 without modifying the positions of the fasteners 628, 636. Accordingly, the exact settings of the fasteners 628, 636 may be preserved when the patient removes or dons the headgear 600 and frame 700. The first and second arm portions 720, 722 are movable from a released position, shown in FIG. 19, to a latched position, shown in FIGS. 15 and 16, by pivoting the first arm portion 720 about the pivotal connection thereof with the frame 712 toward the frame 712 and simultaneously pivoting the second arm portions 722 about its pivotal connection with the first arm portion 720 toward the frame 712. The pivotal movements of the first and second arm portions 720, 722 are in opposite directions relative to one another, as indicated by the arrows in FIG. 19. In an intermediate position (not shown) determined by specific configurations of the first and second arm portions 720, 722, the second arm portions 722 move into an over-center relation with the respective first arm portions 720. Accordingly, when the connecting arms 718 are in their latched positions, shown in FIG. 16, the connecting arms 718 remain in the latched positions without supplementary connecting structures. Moreover, the connecting arms 718 may quickly and easily be moved into the release positions thereof by moving the first and second arm portions 720, 722 past the intermediate over-center position.

Mask Frame Selectively Deformable

Figure 20:
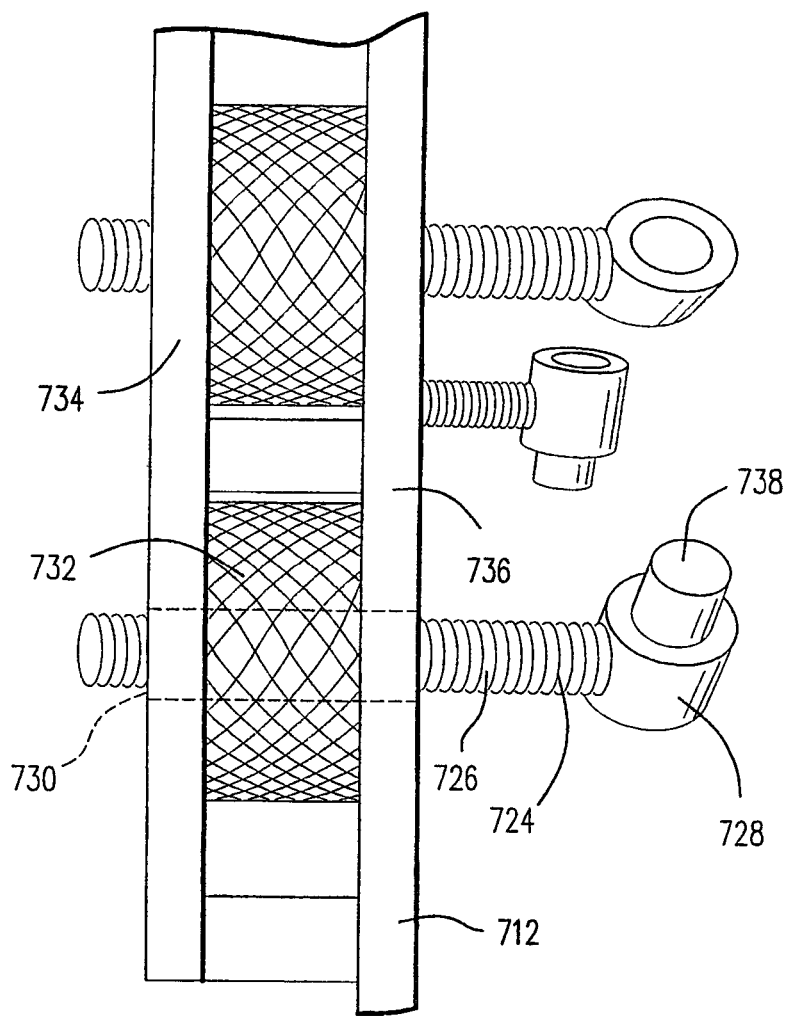
FIG. 20 is a side view of the frame shown in FIG. 15.

As shown in FIGS. 15 and 16, the mask 800 may be formed with a substantially triangular configuration. As also shown, the mask 800 includes an annular, anteriorly extending peripheral flange 802 with which the frame 700 connects. Specifically, the frame 712 includes a plurality of posteriorly extending support members 724. As shown in FIG. 20, the support members 724 have threaded bodies 726 and connecting structures 728 on posterior ends thereof. The threaded bodies 726 extend through bores 730 within the frame 712 and are threadedly engaged with threaded thumb wheels 732. The thumb wheels 732 are positioned between horizontally spaced anterior and posterior wall structures 734, 736 and are retained therebetween. Accordingly, rotation of the thumb wheels 732 serves to advance or retreat the threaded bodies 726 relative to the frame 712. The connecting structures 728 include transversely extending tab members 738 that are received within respective openings 804 within the peripheral flange 802 of the mask 800.

Accordingly, by adjusting the thumb wheels 732, a position of the mask 800, or portions thereof, may be manipulated relative to the frame 712. As the frame 712 may be held relatively constant by the headgear 600 relative to the patient's head, adjustment of the thumb wheels 732 allows substantially fine adjustment of the mask 800 and/or portions thereof relative to the patient's face. Additionally, adjustment between the headgear (i.e., threaded adjusting members 626, 634) and the frame 700 (i.e., connecting portions 702, 706) and between the frame 700 (i.e., support members 724) and the mask 800 (i.e., openings 804) allow the patient to vary the relative positions of the headgear, frame, and mask very easily and in minute increments. In this manner, the patient is able to effect a comfortable fit of the mask and headgear, while ensuring adequate air sealing between the patient's face and the mask to prevent air leaks. Furthermore, the use of the pivotable connecting arms 718, provides a quick-releasing mechanism that eliminates the need for adjusting the relative headgear, frame, and mask positions to don or remove the headgear and mask.

Additional Microadjustment of Headgear

Figure 21:
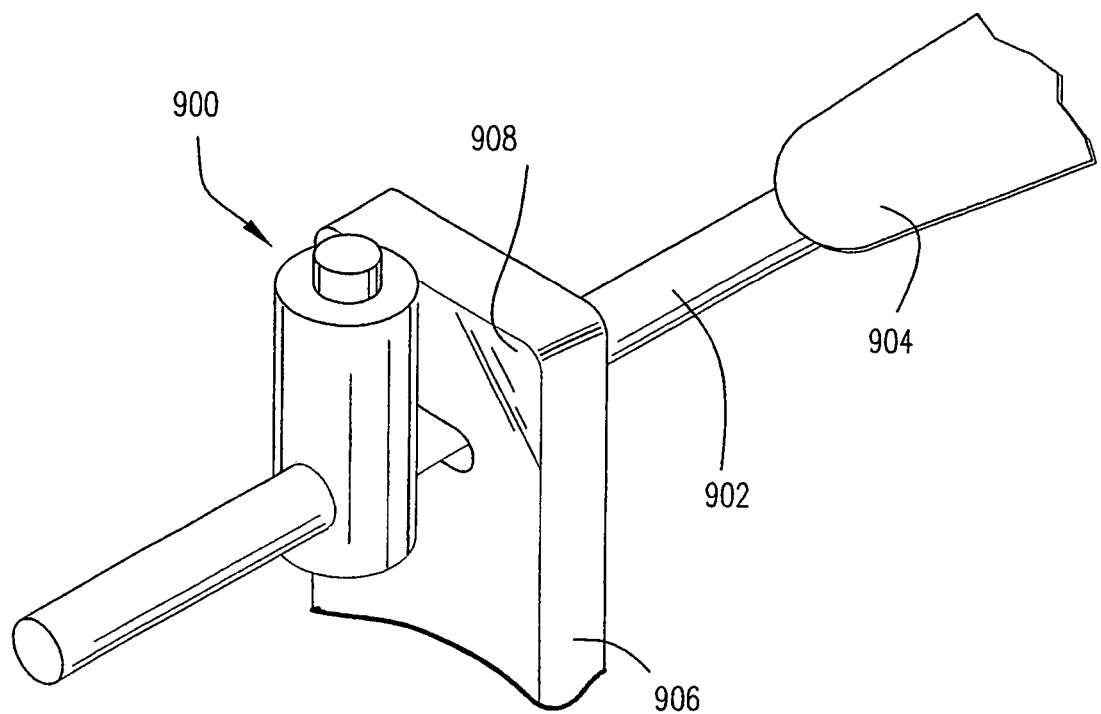
FIG. 21 is a perspective view of a spring clip and elongated member.

FIG. 21 shows an arrangement of a spring clip 900 and elongated member 902 that may be utilized in lieu of the threaded adjusting members 626, 634 and respective fasteners 628, 636. The elongated member 902 extends from an anterior end 904 of one of the strap portions of a headgear, such as a headgear of an embodiment discussed above. It is contemplated that the elongated member 902 may be similar to the threaded adjusting members 626, 634 or may have another configuration, such as circular. It is also contemplated that the elongated member 902 may be a polymer material, such as the threaded adjusting members 626, 634, or may be, e.g., cord or string.

Figure 22:
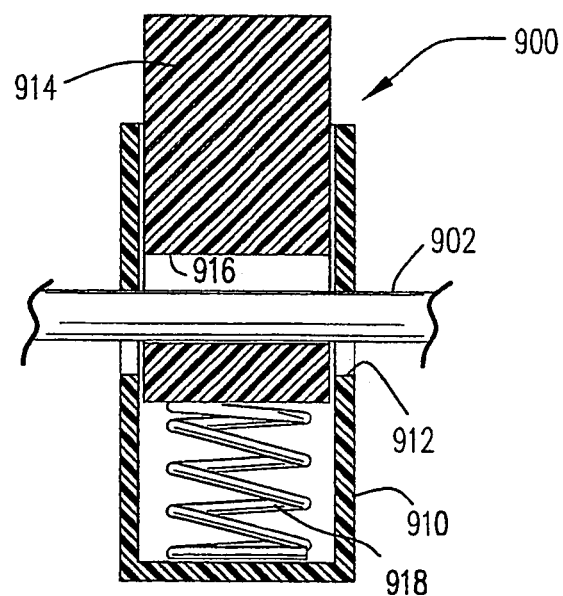
FIG. 22 is a cross-sectional view of the spring clip shown in FIG. 21.

The spring clip 900 is secured to the elongated member 902 at a position thereon anteriorly of a connecting portion 906 of a frame (e.g., connecting portions 702, 706) and abuts an anteriorly facing surface 908 of the connecting portion 906 to maintain a tension within the elongated member 902. As shown in FIG. 22, the spring clip 900 includes a substantially cylindrical housing member 910 that provides a transverse bore 912 therethrough, through which the elongated member 902 may pass. A core member 914 is disposed within an interior of the housing member 910 and has a bore 916 formed therethrough. The core member 914 is biased away from a bottom portion of the housing member 910 by a spring structure 918, which may be a compression spring. The core member 914 is manually displaceable within the housing member 910 to substantially align the bores 912, 916. At this point, the elongated member 902 may be inserted within the bores 912, 916, or a relative longitudinal position of the clip 900 on the elongated member 902 may be altered. Upon release of the manual movement of the core member 914, the core member 914 is moved relative to the housing member 910 by the spring structure 918 until opposing surfaces of the bores 912, 916 engage respective surfaces of the elongated member 902. The spring clip 900 is then secured to the elongated member 902. The elongate member 902 is secured, e.g., by friction and/or engagement of detents. The detents may be ramped to provide ratcheting action, e.g., slide to tighten and push button to release.

Although the above description contains specific examples of the present invention, these should not be construed as limiting the scope of the invention but as merely providing illustrations of some of the presently preferred embodiments of this invention.

The invention claimed is:

1. A mask for use with a CPAP device, comprising:
    a frame; and
    a cushion provided to the frame, the cushion, in cross section, having a generally U-shaped configuration defining a face contacting surface, an inner leg of the U-shaped configuration being proximal to the frame and an outer leg defining a distal end spaced away from the frame, the inner leg defining an opening in the cushion, the opening being adapted to receive pressurized gas from the CPAP device, wherein the U-shaped configuration includes a connecting portion between the inner leg and the outer leg that provides said face contacting surface, and the inner leg extends in a continuous, uninterrupted and smooth manner in a direction of flow of the pressurized gas through the opening.

2. The mask according to claim 1, wherein the inner leg extends to the opening.

3. The mask according to claim 2, wherein at least a portion of the inner leg has a convex shape.

4. The mask according to claim 1, further comprising headgear connectors adapted to connect to headgear.

5. The mask according to claim 4, further comprising headgear adapted to connect to the headgear connectors, the headgear adapted to secure the headgear to a patient's head.

6. The mask according to claim 1, wherein the frame includes an inner peripheral portion that is connected to or otherwise provided to the cushion.

7. The mask according to claim 1, wherein the cushion comprises foam material.

8. The mask according to claim 1, wherein the cushion comprises silicone material.

9. The mask according to claim 1, wherein the cushion extends from the frame and curves generally away from the frame to form the face contacting surface.

10. The mask according to claim 1, wherein the inner and outer legs are generally mirror images of one another.

11. The mask according to claim 1, wherein the outer leg curves outwardly compared to the frame such that a free end portion thereof is directed away from a patient side of the mask and substantially parallel to the inner leg.

12. The mask according to claim 1, wherein the U-shaped configuration defines a recess between the inner and outer legs and positioned opposite to said face contacting surface.

13. The mask according to claim 1, wherein said face contacting surface includes a generally convex configuration adapted to contact the patient's face.

14. The mask according to claim 1, wherein the cushion extending from the outer leg across the connecting portion and to the inner leg has a generally convex shape.

15. A mask for use with a CPAP device, comprising a cushion having a generally U-shaped cross-sectional configuration, the cushion including an inner leg, an outer leg, and a face contacting surface formed between the inner leg and the outer leg, the inner leg defining an opening in the cushion, the opening adapted to receive pressurized gas from the CPAP device, wherein the inner leg extends in a continuous, uninterrupted and smooth manner in a direction of flow of the pressurized gas through the opening.

16. The mask according to claim 15, further comprising a tube portion connected to the opening, the tube portion extending from the supporting portion.

17. The mask according to claim 16, wherein the tube portion is adapted to connect to a pressurized gas conduit.

18. The mask according to claim 15, further comprising headgear connectors adapted to connect to headgear.

19. The mask according to claim 18, further comprising headgear adapted to connect to the headgear connectors, the headgear adapted to secure the headgear to a patient's head.

20. The mask according to claim 15, further comprising a supporting portion adapted to support the cushion.

21. The mask according to claim 15, wherein the cushion comprises foam material.

22. The mask according to claim 15, wherein the cushion comprises silicone.

23. The mask according to claim 15, wherein the outer leg curves outwardly such that a free end portion thereof is directed away from a patient side of the mask and substantially parallel to the inner leg.

24. The mask according to claim 15, wherein the U-shaped configuration defines a recess between the inner and outer legs and positioned opposite to said face contacting surface.

25. The mask according to claim 15, wherein the face contacting surface includes a generally convex configuration adapted to contact the patient's face.

26. The mask according to claim 15, wherein the inner leg extends to the air flow opening.

27. The mask according to claim 15, wherein at least a portion of the inner leg has a convex shape.

28. The mask according to claim 15, wherein the cushion extending from the outer leg across the connecting portion and to the inner leg has a generally convex shape.

* * * * *

UNITED STATES PATENT AND TRADEMARK OFFICE
CERTIFICATE OF CORRECTION

PATENT NO. : 8,522,785 B2
APPLICATION NO. : 10/523607
DATED : September 3, 2013
INVENTOR(S) : Berthon-Jones et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2224 days.

Signed and Sealed this
Fifteenth Day of September, 2015

Michelle K. Lee
*Director of the United States Patent and Trademark Office*